United States Patent
Freeman et al.

(10) Patent No.: US 11,219,737 B2
(45) Date of Patent: ***Jan. 11, 2022

(54) REPERFUSION PROTECTION IN RESUSCITATION

(71) Applicant: ZOLL Medical Corporation, Chelmsford, MA (US)

(72) Inventors: Gary A Freeman, Waltham, MA (US); Annemarie E Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 655 days.

This patent is subject to a terminal disclaimer.

(21) Appl. No.: 16/058,592

(22) Filed: Aug. 8, 2018

(65) Prior Publication Data

US 2018/0344964 A1 Dec. 6, 2018

Related U.S. Application Data

(60) Continuation of application No. 14/527,583, filed on Oct. 29, 2014, now Pat. No. 10,071,218, which is a (Continued)

(51) Int. Cl.
*A61M 16/12* (2006.01)
*A61M 16/00* (2006.01)
*A61M 16/04* (2006.01)

(52) U.S. Cl.
CPC .......... *A61M 16/12* (2013.01); *A61M 16/026* (2017.08); *A61M 2016/0413* (2013.01); *A61M 2202/0225* (2013.01); *A61M 2205/3313* (2013.01); *A61M 2205/502* (2013.01); *A61M 2230/04* (2013.01); *A61M 2230/202* (2013.01);
(Continued)

(58) Field of Classification Search
CPC .. A61M 16/003; A61M 16/103; A61M 16/12; A61M 16/0057; A61H 31/00
See application file for complete search history.

(56) References Cited

U.S. PATENT DOCUMENTS 3,461,860 A 8/1969 Barkalow
4,112,938 A 9/1978 Jeretin
(Continued)

FOREIGN PATENT DOCUMENTS

GB 1565916 4/1980
JP 61-085963 A 5/1986
(Continued)

OTHER PUBLICATIONS

Lurie, K. et al., "Improving the Efficiency of Cardiopulmonary Resuscitation with an Inspiratory Impedance Threshold Valves," Grit Care Med., vol. 28, No. 11, Suppl., pp. N207-N209 2000.
(Continued)

*Primary Examiner* — LaToya M Louis
(74) *Attorney, Agent, or Firm* — Zoll Medical Corporation

(57) ABSTRACT

An apparatus and method for resuscitating a patient suffering from cardiac arrest or another condition in which normal circulation has been interrupted. A ventilator is used for delivering a gas mixture to the patient. The ventilator is configured to adjust the partial pressure of CO2 to one or more partial pressures high enough to slow expiration of CO2 from the patient's lungs and thereby maintain a reduced pH in the patient's tissues for a period of time following return of spontaneous circulation.

40 Claims, 5 Drawing Sheets

Related U.S. Application Data continuation-in-part of application No. 13/020,096, filed on Feb. 3, 2011, now Pat. No. 9,457,165, which is a division of application No. 11/339,307, filed on Jan. 24, 2006, now abandoned.

(52) U.S. Cl.
CPC . *A61M 2230/205* (2013.01); *A61M 2230/208* (2013.01); *A61M 2230/432* (2013.01)

(56) References Cited

U.S. PATENT DOCUMENTS

| | | | |
|---|---|---|---|
| 4,198,963 A | 4/1980 | Barkalow et al. | |
| 4,867,152 A | 9/1989 | Kou et al. | |
| 5,320,093 A | 6/1994 | Raemer | |
| 5,402,796 A | 4/1995 | Packer et al. | |
| 5,664,563 A | 9/1997 | Schroeder et al. | |
| 5,743,259 A | 4/1998 | Kruse et al. | |
| 5,778,872 A | 7/1998 | Fukunaga et al. | |
| 5,813,403 A | 9/1998 | Soller et al. | |
| 6,055,447 A | 4/2000 | Weil et al. | |
| 6,461,315 B1 | 10/2002 | Gattinoni | |
| 6,564,088 B1 | 5/2003 | Soller et al. | |
| 6,612,308 B2 | 9/2003 | Fisher et al. | |
| 6,622,725 B1 | 9/2003 | Fisher et al. | |
| 6,766,188 B2 | 7/2004 | Soller | |
| 6,799,570 B2 | 10/2004 | Fisher et al. | |
| 6,951,216 B2 | 10/2005 | Heinonen | |
| 7,100,606 B2 | 9/2006 | Fisher et al. | |
| 7,886,740 B2 | 2/2011 | Thomas et al. | |
| 7,967,756 B2 | 6/2011 | Stahmann et al. | |
| 7,970,470 B2 | 6/2011 | Hartley et al. | |
| 8,355,899 B2 | 1/2013 | Gerder-Kallisch et al. | |
| 2002/0087057 A1 | 7/2002 | Lovejoy et al. | |
| 2005/0124866 A1 | 6/2005 | Elaz et al. | |

FOREIGN PATENT DOCUMENTS

| | | |
|---|---|---|
| JP | 2000-511531 | 9/2000 |
| JP | 2002-306432 | 10/2002 |
| WO | 97/43899 A1 | 11/1997 |
| WO | 2004069317 A1 | 8/2004 |
| WO | 2004112683 A1 | 12/2004 |

OTHER PUBLICATIONS

Povoas et al., Electrocardiographic Waveform Analysis for Predicting the Success of Defibirllation, Grit Care Med, vol. 28, No. 11, Suppl., pp. N210-N211 2000.

REPERFUSION PROTECTION IN RESUSCITATION

CROSS-REFERENCE TO RELATED APPLICATION

This application is a continuation-in-part of, and claims priority to, U.S. application Ser. No. 13/020,096, filed on Feb. 3, 2011, which is a divisional application of and claims priority to U.S. application Ser. No. 11/339,307, filed on Jan. 24, 2006, each of which is incorporated by reference herein in its entirety for all purposes.

TECHNICAL FIELD

This invention relates to ventilatory support devices for use in cardiac arrest.

BACKGROUND

Cardiac Arrest, or Sudden Death, is a descriptor for a diverse collection of physiological abnormalities with a common cardiac aetiology, wherein the patient typically presents with the symptoms of pulselessness, apnoea, and unconsciousness. Cardiac arrest is widespread, with an estimated 300,000 victims annually in the U.S. alone and a similar estimate of additional victims worldwide. Early defibrillation is the major factor in sudden cardiac arrest survival. There are, in fact, very few cases of cardiac arrest victims saved which were not treated with defibrillation. There are many different classes of abnormal electrocardiographic (ECG) rhythms, some of which are treatable with defibrillation and some of which are not. The standard terminology for this is "shockable" and "non-shockable" ECG rhythms, respectively. Non-shockable ECG rhythms are further classified into hemodynamically stable and hemodynamically unstable rhythms. Hemodynamically unstable rhythms are those which are incapable of supporting a patient's survival with adequate blood flow (non-viable). For example, a normal sinus rhythm is considered non-shockable and is hemodynamically stable (viable). Some common ECG rhythms encountered during cardiac arrest that are both non-shockable and hemodynamically unstable are: bradycardia, idioventricular rhythms, pulseless electrical activity (PEA) and asystole. Bradycardias, during which the heart beats too slowly, are non-shockable and also possibly non-viable. If the patient is unconscious during bradycardia, it can be helpful to perform chest compressions until pacing becomes available. Idioventricular rhythms, in which the electrical activity that initiates myocardial contraction occurs in the ventricles but not the atria, can also be non-shockable and non-viable (usually, electrical patterns begin in the atria). Idioventricular rhythms typically result in slow heart rhythms of 30 or 40 beats per minute, often causing the patient to lose consciousness. The slow heart rhythm occurs because the ventricles ordinarily respond to the activity of the atria, but when the atria stop their electrical activity, a slower, backup rhythm occurs in the ventricles. Pulseless Electrical Activity (PEA), the result of electro-mechanical dissociation (EMD), in which there is the presence of rhythmic electrical activity in the heart but the absence of myocardial contractility, is non-shockable and non-viable and would require chest compressions as a first response. Asystole, in which there is neither electrical nor mechanical activity in the heart, cannot be successfully treated with defibrillation, as is also the case for the other non-shockable, non-viable rhythms. Pacing is recommended for asystole, and there are other treatment modalities that an advanced life support team can perform to assist such patients, e.g. intubation and drugs. The primary examples of shockable rhythms that can be successfully treated with defibrillation are ventricular fibrillation, ventricular tachycardia, and ventricular flutter.

Normally, electrochemical activity within a human heart causes the organ's muscle fibers to contract and relax in a synchronized manner. This synchronized action of the heart's musculature results in the effective pumping of blood from the ventricles to the body's vital organs. In the case of ventricular fibrillation (VF), however, abnormal electrical activity within the heart causes the individual muscle fibers to contract in an unsynchronized and chaotic way. As a result of this loss of synchronization, the heart loses its ability to effectively pump blood. Defibrillators produce a large current pulse that disrupts the chaotic electrical activity of the heart associated with ventricular fibrillation and provides the heart's electrochemical system with the opportunity to re-synchronize itself. Once organized electrical activity is restored, synchronized muscle contractions usually follow, leading to the restoration of effective cardiac pumping.

First described in humans in 1956 by Dr. Paul Zoll, transthoracic defibrillation has become the primary therapy for cardiac arrest, ventricular tachycardia (VT), and atrial fibrillation (AP). Monophasic waveforms dominated until 1996, when the first biphasic waveform became available for clinical use. Attempts have also been made to use multiple electrode systems to improve defibrillation efficacy. While biphasic waveforms and multiple-electrode systems have shown improved efficacy relative to monophasic defibrillation, there is still significant room for improvement: shock success rate for ventricular fibrillation (VF) remains less than 70% even with the most recent biphasic technology. In these cases, shock success was defined to be conversion of a shockable rhythm into a non-shockable rhythm, including those non-shockable rhythms which are also non-viable. Actual survival-to-hospital-discharge rates remain an abysmal ten percent or less. Survival rates from cardiac arrest remain as low as 1-3% in major U.S. cities, including those with extensive, advanced prehospital medical care infrastructures.

Approximately 40-50% of cardiac arrest victims are resuscitated by paramedics and emergency medical technicians (EMTs) in the field and brought to the hospital for further treatment; however, due to the insult on the victim's vital organs from the cardiac arrest, typically only about 25% (or approximately 40,000 out of 600,000 cardiac arrest victims, worldwide) of those victims who survive to the hospital will survive to being discharged from the hospital.

The treatment window for cardiac arrest with current treatments of defibrillation, cardiopulmonary resuscitation, and inotropic (e.g. epinephrine) drug treatment is very narrow. Long term survival rates from the time of victim collapse decrease at a roughly exponential rate with a time constant of roughly 2 minutes. Thus, just two minutes of delay in treatment using the currently recommended treatment protocols result in a long term survival rate of 30-35%. After 15 minutes, the long term survival rates are below 5%. While the response times of emergency medical systems have improved significantly over the last quarter century to the point that average times from emergency call to arrival at the victim is typically 9 minutes or less, bystander delays in making the emergency call typically add 2-3 minutes to the total arrest time, for a total of 11-12 minutes. In addition, the bystander making the emergency call may not even have witnessed the cardiac arrest, which may have occurred at some point in the past. Unwitnessed arrest accounts for at least half of all cardiac arrests. Cardiac arrest downtimes are only reported for witnessed arrests; it has been estimated, however, that if unwitnessed arrests were to be included, the average downtime for all victims would exceed 15 minutes. At the time of initial collapse, the ECGs of nearly all cardiac arrest victims are shockable rhythms such as VF or VT; after 15 minutes, however, the ECG rhythms of most cardiac arrest victims have degenerated into the non-shockable rhythms of PEA or asystole. Attempts to reduce this response time through the widespread adoption of AEDs has been minimally successful, at best, for a variety of economic and social factors. It would be thus advantageous to have treatment methods available to deal with cardiac arrest victims with profound ischemia due to long downtimes.

During cardiac arrest, cerebral blood flow ceases and global cerebral hypoxic-ischemic injury begins within minutes. Myocardial and neuronal tissue is able to remain viable during prolonged periods of ischemia—as long as twenty minutes, but paradoxically will sustain immediate damage during the return of circulation and oxygenation. It has been shown in a variety of studies at the tissue-level and animal model that successful resuscitation with return of spontaneous circulation (ROSC) leads to a secondary cascade of injury related to reperfusion injury. This reperfusion injury is particularly acute in neuronal tissue. When neurons and myocytes shift to anaerobic metabolism as a result of oxygen depletion, during the course of ATP hydrolysis lactate is converted to lactic acid, H+ is generated, and intracellular pH drops. This activates the sodium/hydrogen (NaH) exchange ion channels, which, however, require ATP and thus become depressed during ischemia. There is thus a build-up of intracellular H+ during ischemia. During reperfusion, the NaH exchange channel is reactivated causing a net influx of sodium which then causes a net influx of calcium via the sodium/calcium (NCX) exchange channel in order to exteriorize the elevated sodium ions. Elevation of intracellular calcium can lead to an accumulation of this ion by mitochondria, with activation of mitochondrial permeability transition (MPT).

During reperfusion, intracellular levels of glutamate, an excitatory neurotransmitter released from presynaptic terminals, increases markedly. Glutamate activates ion channel complexes, particularly the N-methyl-D-aspartate (NMDA) receptors, which when activated increase calcium conductance from the extracellular to intracellular fluid. Mitochondrial calcium increases, resulting in the formation of reactive oxygen species. Both mitochondrial calcium overload and ROS production initiate the formation of large pores in the mitochondrial membrane. Opening of high-conductance mitochondrial transition pores (MTP) in the mitochondrial inner membrane initiates onset of the mitochondrial permeability transition (MPT). The MTP pores conduct both positively and negatively charged solutes of up to 1,500 Da. Pore opening causes the collapse of mitochondrial membrane potential and cessation of mitochondrial ATP production. In addition, multiple biochemical cascades lead to the production of oxygen free-radicals and the activation of proteases, endonucleases, phospholipases and xanthine oxidase which cause destruction of cell membranes and other essential cytoskeletal structures such as microtubules. Even if these events are not immediately fatal to the cell, some neurons later undergo programmed cell death (apoptosis).

After successful cardiac resuscitation and ROSC, cerebral blood flow may remain abnormally low for several hours. After an initial hyperemia resulting from high circulating levels of catecholamines, cerebral blood flow decreases just as the cerebral metabolic rate for oxygen increases. This can lead to a prolonged state of relative cerebral ischemia. This prolonged mismatch between cerebral metabolic rate and blood is flow, and ongoing biochemical and molecular processes related to delayed neuronal apoptotic and necrotic cell death, provide the scientific rationale for induced hypothermia as a form of neuroprotection after cardiac arrest. One method developed is the cooling of comatose cardiac arrest survivors to approximately 34 degrees Celsius within 4 hours of arrest onset. The exact mechanism for the therapeutic effects of hypothermia is not fully understood, but has been shown in several studies to enhance the survival rates of patients who are initially resuscitated (the approximately 40-50% of victims making it to the hospital). Hypothermia is common in the cardiac intensive care, hospital environment such as in bypass operations, etc, but there are two related drawbacks of hypothermia which have prevented its widespread use in the pre-hospital environment.

The first of these drawbacks is the primary biomedical engineering challenge of hypothermia: the large thermal mass of the victim and the difficulty of cooling the victim quickly and safely. While it has been shown that hypothermia is beneficial as long as it is applied within 4 hours of cardiac arrest, studies have also shown that cooling prior to resuscitation provides additive therapeutic benefits. While the causes for this are only speculative, one of the factors is likely the positive effects of hypothermia during the reperfusion phase of resuscitation. Practically speaking, it is highly undesirable to delay defibrillation and resuscitation to cool a patient to the proper temperature. Non-invasive methods of cooling take at minimum 10 minutes to 1 hour, while invasive methods such as extraction and cooling of the blood may take only 3-5 minutes, but are hazardous to the patient, particularly in the pre-hospital environment. In the case of defibrillation, even a delay of 3 minutes can result in a decrease in survival of 30%. While hypothermia may be effective at counteracting longer-term deleterious effects of ischemia and reperfusion, it would be desirable to have a treatment that can provide immediate protective effects against reperfusion injury while, at the same time, not delaying any current resuscitation interventions.

The mechanisms allowing prolonged cell survival during ischemia and minimizing lethal cell injury after reperfusion remain incompletely understood. It has been shown in studies that the naturally occurring acidosis of ischemia, like hypothermia, strongly protects renal cells, myocytes, and hepatocytes against ischemia-induced cell death. In contrast, the return of extracellular pH to physiological levels is an event that actually precipitates lethal cell injury, termed the "pH paradox". It has been hypothesized by researchers that the pH dependency of reperfusion injury may be the consequence of the pH dependency of the MTP opening. Conductance of the NMDA channel is also known to decrease steeply when extracellular pH is reduced below 7.0. Intracellular pH may also be important; intracellular acidosis during and after simulated ischemia and reperfusion has been shown to protect cultured cardiac myocytes against injury. Increased extracellular proton concentration will also minimize the inward sodium influx via the Na—H exchange ion channels, thereby reducing the intracellular sodium concentrations and the net influx of calcium via the sodium-calcium exchanger channels, and thus minimizing calcium overload.

Ventilation is a key component of cardiopulmonary resuscitation during treatment of cardiac arrest. Venous blood returns to the heart from the muscles and organs depleted of oxygen ($O_2$) and full of carbon dioxide ($CO_2$). Blood from various parts of the body is mixed in the heart (mixed venous blood) and pumped to the lungs. In the lungs the blood vessels break up into a net of small vessels surrounding tiny lung sacs (alveoli). The net sum of vessels surrounding the alveoli provides a large surface area tier the exchange of gases by diffusion along their concentration gradients. A concentration gradient exists between the partial pressure of $CO_2$ ($PCO_2$) in the mixed venous blood ($PvCO_2$) and the alveolar $PCO_2$. The $CO_2$ diffuses into the alveoli from the mixed venous blood from the beginning of inspiration until an equilibrium is reached between the $PvCO_2$ and the alveolar $PCO_2$, at some time during the breath. When the subject exhales, the first gas that is exhaled comes from the trachea and major bronchi which do not allow gas exchange and therefore will have a gas composition similar to the inhaled gas. The gas at the end of this exhalation is considered to have come from the alveoli and reflects the equilibrium $CO_2$ concentration between the capillaries and the alveoli; the $PCO_2$ in this gas is called end-tidal $PCO_2$ ($PE_1CO_2$).

When the blood passes the alveoli and is pumped by the heart to the arteries it is known as the arterial $PCO_2$ ($PaCO_2$)). The arterial blood has a $PCO_2$ equal to the $PCO_2$ at equilibrium between the capillaries and the alveoli. With each breath some $CO_2$ is eliminated from the lung and fresh air containing little or no $CO_2$ ($CO_2$ concentration is assumed to be 0) is inhaled and dilutes the residual alveolar $PCO_2$, establishing a new gradient for $CO_2$ to diffuse out of the mixed venous blood into the alveoli. The rate of breathing, or minute ventilation (V), usually expressed in L/min, is exactly that required to eliminate the $CO_2$ brought to the lungs and maintain an equilibrium $PCO_2$ (and $PaCO_2$) of approximately 40 mmHg (in normal humans). When one produces more $CO_2$ (e.g., as a result of fever or exercise), more $CO_2$ is produced and carried to the lungs. One then has to breathe harder (hyperventilate) to wash out the extra $CO_2$ from the alveoli, and thus maintain the same equilibrium $PaCO_2$. But if the $CO_2$ production stays normal, and one hyperventilates, then the $PaCO_2$ falls. Conversely, if $CO_2$ production stays constant and ventilation falls, arterial $PCO_2$ rises. Some portion of the inspired air volume goes to the air passages (trachea and major bronchi) and alveoli with little blood perfusing them, and thus doesn't contribute to removal of $CO_2$ during exhalation. This portion is termed "dead space" gas. That portion of V that goes to well-perfused alveoli and participates in gas exchange is called the alveolar ventilation (VA) and exhaled gas that had participated in gas exchange in the alveoli is termed "alveolar gas".

Monitoring and control of ventilation parameters as a function of measured expiratory $CO_2$ is commonly used in ventilation systems. U.S. Pat. No. 4,112,938 describes a respirator that uses measurement of alveolar gas $CO_2$ partial pressure as a means of adjusting a reservoir size to control inspiratory $CO_2$ concentration. U.S. Pat. No. 5,320,093 describes a ventilator that adjusts inspiratory $CO_2$ concentration so as to enhance a patient's natural ventilatory drive during recovery from anesthesia. In U.S. Pat. No. 5,402,796, a method is described which provides better accuracy of $PaCO_2$ utilizing an initial calibration sample. U.S. Pat. Nos. 5,778,872, 6,612,308B2 and 6,799,570B2 portable ventilators that use reservoirs to store exhaled air for later use in rebreathing during inspiration so as to keep $CO_2$ levels constant ("isocapnia"). U.S. Pat. No. 6,612,308B2 is further refined in U.S. Pat. No. 6,622,725B1 by providing a method for separating out the alveolar gas from the dead space gas, thus concentrating the expiratory $CO_2$ for later rebreathing. U.S. Pat. No. 6,951,216B2 describes a ventilator utilizing a space-efficient $CO_2$ exchanger that absorbs and stores expiratory $CO_2$ gas that is later released into the inpsiratory gas stream to enhance $CO_2$ concentrations.

SUMMARY

In general, the invention features an apparatus and method for resuscitating a patient suffering from cardiac arrest or another condition in which normal circulation has been interrupted. A ventilator is used for delivering a gas mixture to the patient. The ventilator is configured to adjust the partial pressure of CO2 to one or more partial pressures high enough to slow expiration of CO2 from the patient's lungs and thereby maintain a reduced pH in the patient's tissues for a period of time following return of spontaneous circulation.

In preferred implementations, one or more of the following features may be incorporated. The partial pressure of $CO_2$ may be adjusted to be higher than ambient $CO_2$ partial pressure during the period of time. Adjustment of the partial pressure of $CO_2$ may include adding $CO_2$ to the gas inspired by the patient. The apparatus may comprise a sensor and associated processing for measuring a physiological status of the patient, wherein the partial pressure of $CO_2$ may be adjusted at least in part in response to the output of the sensor. The sensor and associated processing may be configured to detect return of spontaneous circulation, and wherein the partial pressure of $CO_2$ may be changed in response to detection of return of spontaneous circulation. The period of time may be greater than 30 seconds. The period of time may be greater than 3 minutes. The sensor may comprise a $CO_2$ sensor. Adjustment of the partial pressure of $CO_2$ may have the effect of maintaining the pH of the patient's tissues below 7.0 for the period of time following return of spontaneous circulation. The pH of the patient's tissues may be maintained below 6.8. The pH of the patient's tissues may be maintained below 6.5. The apparatus may further comprise a defibrillator, a chest compressor, an infuser, and/or a sensor and associated processing for determining the pH of the patient's tissue, wherein the partial pressure of $CO_2$ may be adjusted at least in part in response to the pH of the patient's tissue. The partial pressure of $CO_2$ may be adjusted to maintain tissue pH below 6.8 for a period of time following return of spontaneous circulation. The partial pressure of $CO_2$ may be gradually lowered over at least a portion of the period of time so as to gradually raise the pH of the patient's tissues. The apparatus may further comprise processing using a mathematical model of the relationship between $CO_2$ retention in the patient and the pH of the patient's tissues. The mathematical model may comprise processing using the Henderson-Hasselbalch equations. The apparatus may further comprise apparatus and processing for measuring the inspired volume and expired volume of $CO_2$ in the ventilation cycle, and using the inspired and expired volumes to adjust the partial pressure of $CO_2$ and apparatus and processing for monitoring an $E_tCO_2$ level, and wherein the partial pressure of $CO_2$ may be adjusted to maintain the $E_tCO_2$ level above a level found in the arrest victim prior to the arrest. The adjustment of the partial pressure of $CO_2$, may be accomplished by adjusting the partial pressure between a lower level in a first cycle and a higher level in a second cycle, wherein in the first cycle the partial pressure of $CO_2$ may be lower than a previously measured $E_tCO_2$ level, and wherein in the second cycle the partial pressure of $CO_2$ may be higher than the previously measured $E_tCO_2$ level, and wherein the lower and higher levels may be adjusted to maintain $E_tCO_2$ at a desired level. The ventilator and chest compressor may be controlled so that a ratio of chest compression rate to ventilation rate is less than 15:2 during at least a portion of the period of time following return of spontaneous circulation. The ratio may be less than 5:1. The ratio may be about 6:2. The apparatus may further comprise a fluid infusion device. The fluid infusion device may be configured to infuse fluids containing metabolic substances during reperfusion. The metabolic substances may comprise amino acids. The amino acids may comprise aspartate, dihydroxyacetone phosphate or glutamate. The apparatus may further comprise a defibrillator, compressor, and infuser. The defibrillator, compressor, ventilator, and infuser may be separate devices and may be linked by a communications link. An additional computing device may be used to synchronize all of the separate devices. There may be both negative and positive pressures available from the ventilator. The ventilator may be configured to elevate oxygen levels to greater than 40%. The period of time may begin prior to the return of spontaneous circulation. The period of time may begin immediately prior to the return of spontaneous circulation.

Other features and advantages of the invention will be apparent from the description and drawings, and from the claims.

DETAILED DESCRIPTION

There are a great many different implementations of the invention possible, too many to possibly describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Some implementations may reduce reperfusion injury by maintaining a low tissue pH during the time period immediately prior to and from 0-60 minutes subsequent to the return of spontaneous circulation (ROSC) by means of addition of carbon dioxide to the inspiratory gases while at the same time increasing oxygen content relative to normal room air concentrations to enhance oxygenation of the brain, heart and other vital organs.

Figure 1:
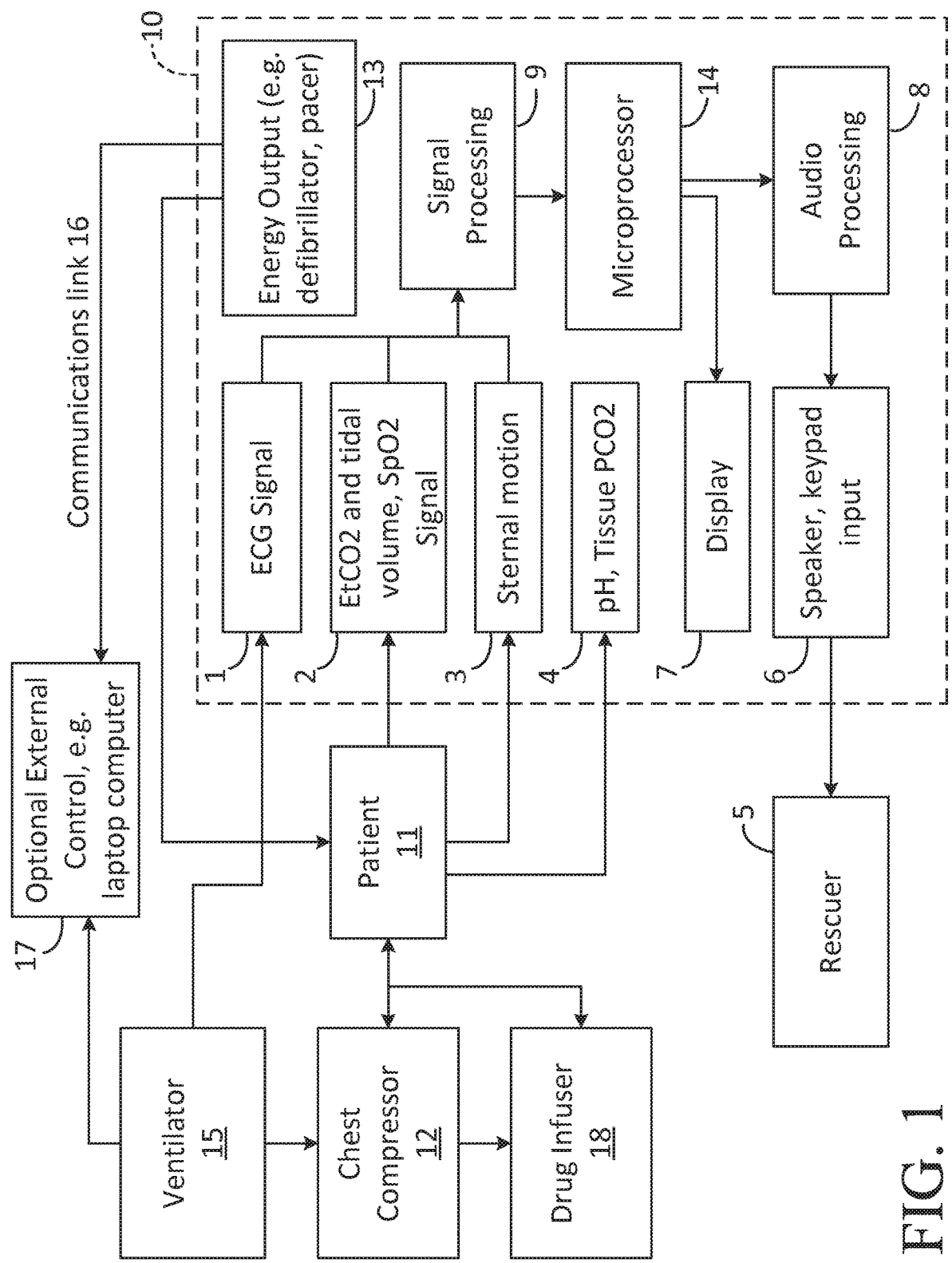
FIG. 1 is the system block diagram of one implementation of one aspect of the invention, including a ventilator integrated with a mechanical chest compression device and a defibrillator.
Figure 2:
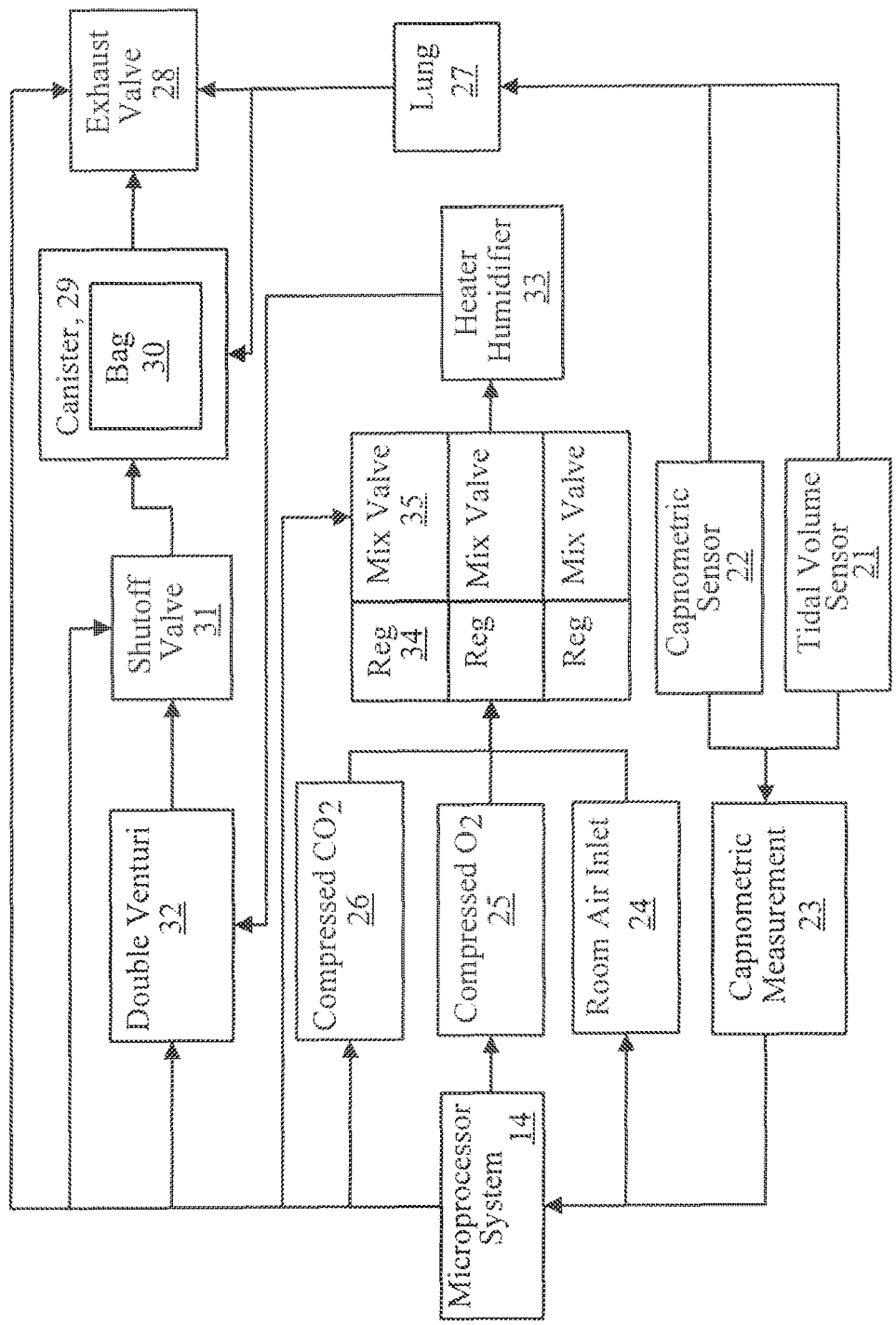
FIG. 2 is a block diagram of the ventilator if FIG. 1.

Referring to FIGS. 1 and 2, the block diagram in FIG. 1 shows an integrated resuscitation system (IRS) with components designed to address various aspects of a resuscitation: defibrillator 13, mechanical compressor 12, and ventilator 15. By control of the partial pressures of the ventilation gases (particularly oxygen), ambient air, and carbon dioxide via the mixing valves 35, the IRS can maintain a patient's tissue pH at approximately the below normal level present immediately prior to ROSC.

The tissue pH is controlled by the following well known physiological mechanism. The transport of $CO_2$ can have a significant impact on the acid-base status of the blood and tissues. The lung excretes over 10,000 molar equivalents of carbonic acid per day compared to less than 100 molar equivalent of fixed acids by the kidneys. Therefore, by altering alveolar ventilation and the elimination of $CO_2$, the acidity of the tissues of the brain, heart, gut and other organs can be modified. $CO_2$ is carried in the blood in three forms: dissolved, as bicarbonate, and in combination with proteins such as carbamino compounds. In solution, carbon dioxide hydrates to form carbonic acid:

$$CO_2 + H_2O \leftrightarrow H_2CO_3$$

The largest fraction of carbon dioxide in the blood is in the form of bicarbonate ion, which is formed by ionization of carbonic acid:

$$H_2CO_3 \leftrightarrow H^+ + HCO_3^- \leftrightarrow 2H^+ + CO_3^{2-}$$

Using the law of mass action, the Henderson-Hasselbalch equation is derived:

$$[H^+] = K_1'[H_2CO_3]/[HCO_3^-], \text{ or}$$

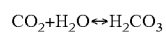

$$[H+] = K'(\alpha P_{CO2})/[HCO_3^-],$$

where $\alpha P_{CO2}$ is the total concentration of $CO_2$ and $H_2CO_3$. The log form of the Hasselbalch equation takes the form:

$$pH = pK_A + \log(HCO_3^-)/(0.03 P_{CO2}),$$

where $K_A$ is the dissociation constant of carbonic acid, equal to 6.1.

Normal $HCO_3^-$ concentration is 24 mmol/liter, with a resultant pH of 7.4. During total ischemia induced by cardiac arrest or trauma, pH will fall to below 7, and commonly in the range of 6.5-6.8, as a result of increasing levels of $CO_2$. At the resumption of circulation and gas exchange in the alveoli, the end-tidal carbon dioxide ($E_tCO_2$) value, as measured by the commonly used capnograph or capnometer, increases rapidly from a value typically below 10 mmHg found during arrest to a supranormal value of 50-75 mmHg—normal values are approximately 35 mmHg—as the body attempts to reduce its $CO_2$ levels.

Figure 3A:
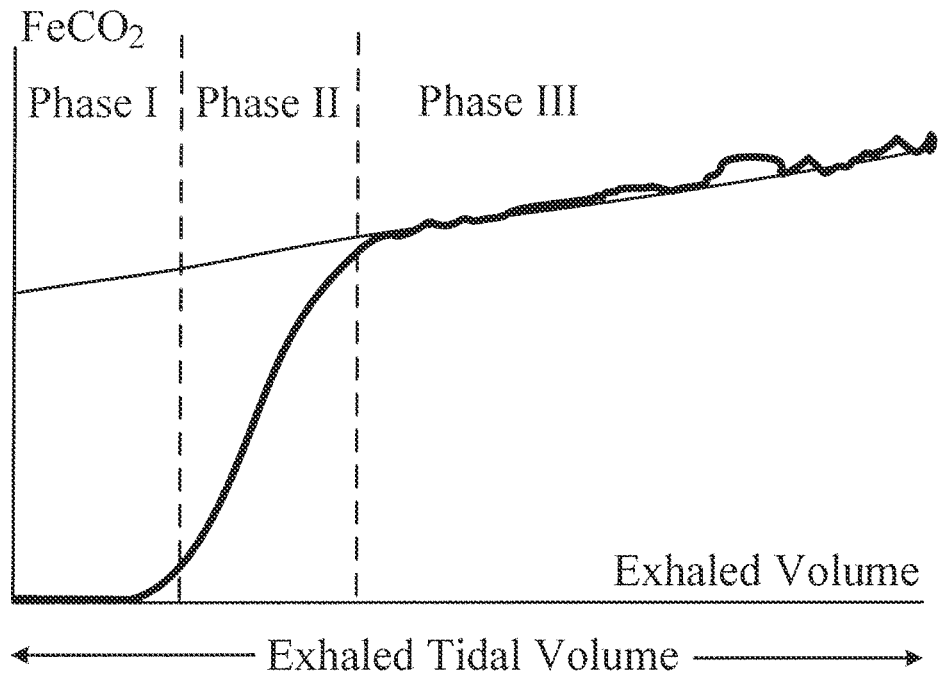
FIGS. 3A and 3B are plots depicting a typical end-tidal capnographic measurement curve.
Figure 3B:
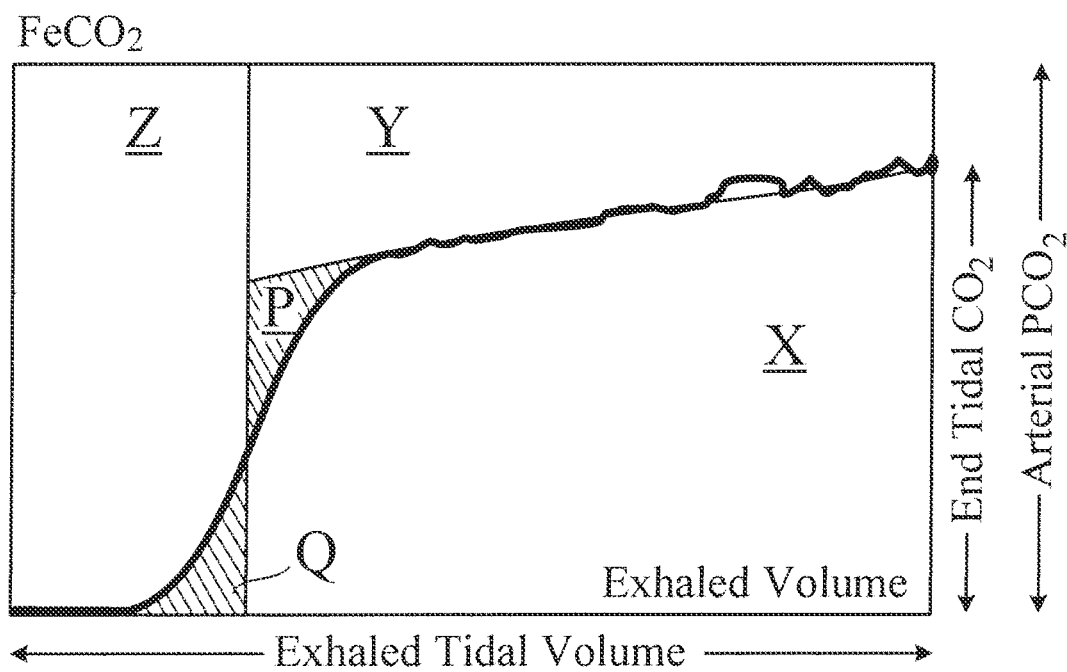

Referring to FIGS. 3A and 3B, phase I represents airway dead space. It is the $CO_2$-free portion of the exhaled breath from the conducting airways. Phase II represents the mixing of airway dead space gas with alveolar gas and is characterized by a significant rise in $CO_2$. Phase III represents alveolar volume. The plateau reflects the level of effective ventilation in the alveoli. Two lines are constructed on the graph; one on the slope of Phase III and the other such that areas p and q are equal.

Airway dead space is measured from the start of expiration to the point where the vertical line crosses the exhaled volume axis. The volume of $CO_2$ in the breath is equal to area X, the total area under the curve. Adding individual breath volumes allows minute $CO_2$ elimination to be calculated in ml/min. Physiologic Vd/Vt as well as physiologic and alveolar dead space can also be calculated if arterial $PCO_2$ is known. A line representing the arterial $PCO_2$ value is constructed parallel to the exhaled volume axis creating areas Y and Z. Area X represents the volume of $CO_2$ in the exhaled tidal volume. Areas Y and Z represent wasted ventilation due to alveolar and airway dead space respectively.

Figure 4A:
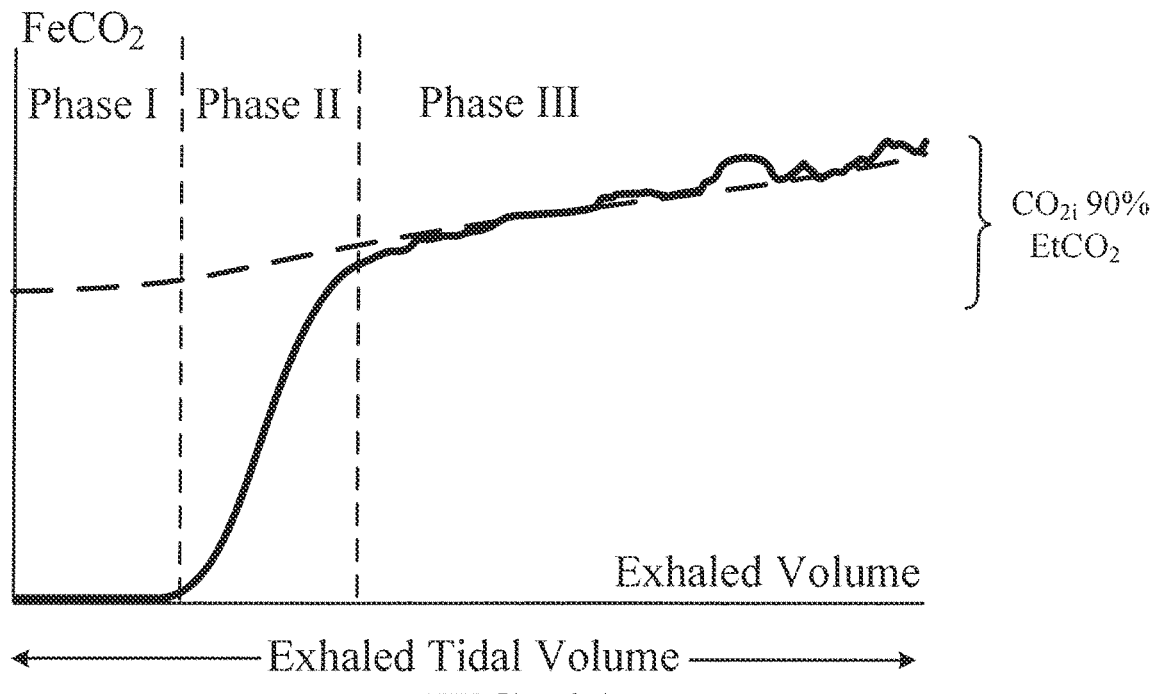
FIGS. 4A and 4B are plots depicting the end-tidal capnographic curve (dotted line) with elevated levels of inspired $CO_2$.
Figure 4B:
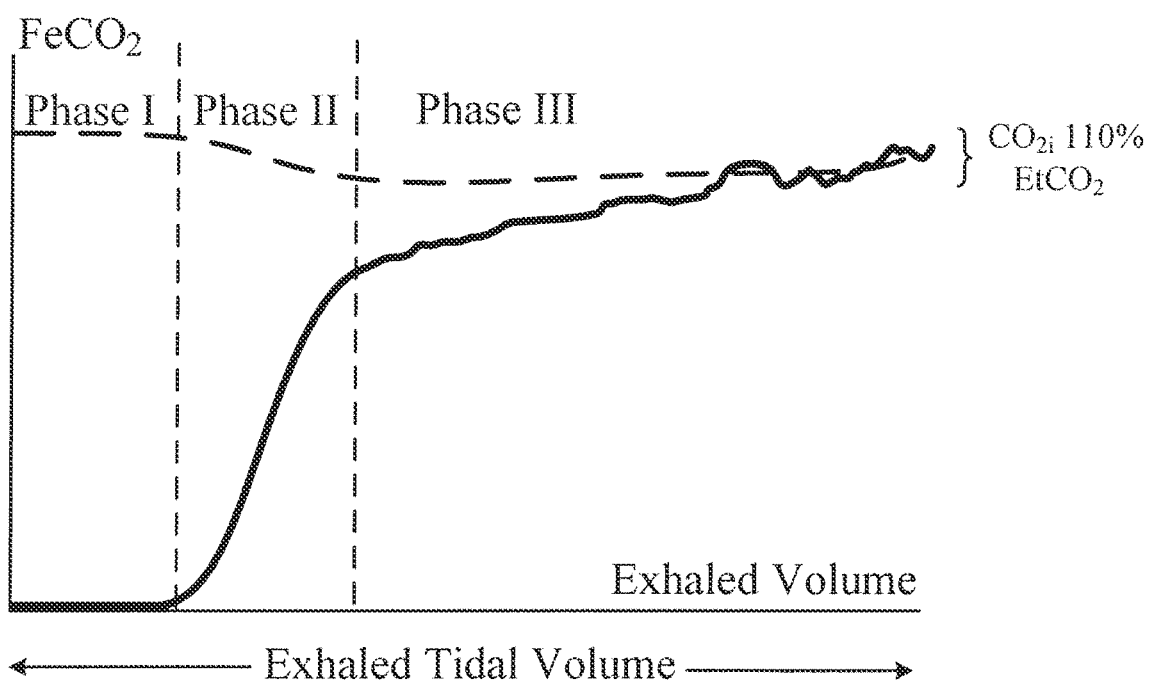
Figure 5:
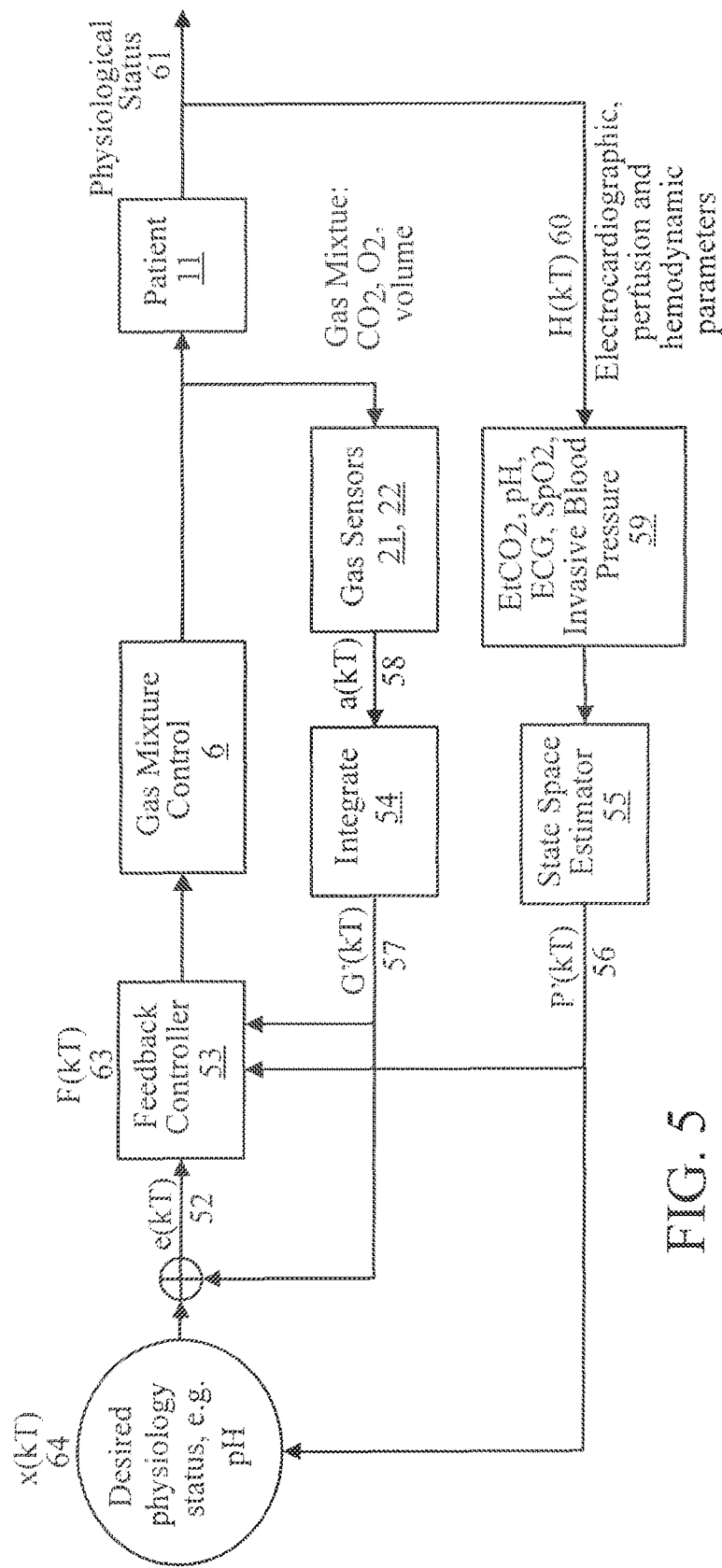
FIG. 5 is a block diagram of a gas mixture control loop of the implementation of FIG. 1.

Referring to FIGS. 1, 4A and 4B, and the flowchart in FIG. 5, the processing unit 14, made up of an electronic processor such as a microprocessor as well as memory and support logic, first determines that a cardiac arrest is in progress, by one or a combination of such known techniques as: (1) electrocardiographic (ECG) analysis to determine whether the ECG is a rhythm due to ventricular fibrillation, ventricular tachycardia, PEA or asystole or a rhythm of supraventricular origin such as a normal sinus rhythm; (2) analysis of the transthoracic impedance signal to determine whether there is blood flow; or (3) simply by means of an input via the user interface 6 by the rescuer 5 indicating that an arrest is in progress. If an arrest is determined to be in progress, the inspiratory gas mixture is adjusted via electronically-controlled flow valves 35 in the differential flow control (DFC) subunit to be predominantly oxygen (60-100%). Once in the CARDIAC ARREST state, the processing unit 14 will wait for input that defines ROSC. This input may be as simple as an input via the user interface by the rescuer that ROSC has occurred, though preferably the input includes a capnometric signal measuring end tidal $CO_2$ ($E_tCO_2$) values 2 in the expired air. When the processing unit 14 detects an increase of more than 30% of the baseline cardiac arrest $E_tCO$ value in 30 seconds and a value greater than 25 mmHg, the processing unit 14 will enter the ROSC state, and begin the process of adding $CO_2$ to the inspired gas mixture.

In other implementations, either the tissue $CO_2$ or pH are measured by such methods as disclosed in U.S. Pat. No. 6,055,447, which describes a sublingual tissue $CO_2$ sensor, or U.S. Pat. Nos. 5,813,403; 6,564,088; and 6,766,188; which describe a method and device for measuring tissue pH via near infrared spectroscopy (NIRS). Each of these patents (U.S. Pat. Nos. 6,055,447; 5,813,403; 6,564,088; and 6,766,188) is hereby expressly incorporated herein by reference in its entirety for all purposes. NIRS technology allows the simultaneous measurement of tissue $PO_2$, $PCO_2$, and pH. One drawback of previous methods for the measurement of tissue pH is that the measurements provided excellent relative accuracy for a given baseline measurement performed in a series of measurements over the course of a resuscitation, but absolute accuracy was not as good, as a result of patient-specific offsets such as skin pigment. One of the benefits of the currently-described implementations is that they do not require absolute accuracy of these pH measurements, only that the offset and gain be stable over the course of the resuscitation. Because tissue pH responds slowly over the course of multiple ventilation cycles, it is used primarily to augment control of $E_tCO_2$ levels by adjusting $CO_{2i}$ with the goal of regulating tissue pH per the following regimen: (1) during the first 5 minutes following ROSC, the pH should remain flat; (2) during the time period of 5-10 minutes, the tissue pH should increase no more than 0.4 pH units/minute, and should be limited to not increase above an absolute number of 6.8; and (3) during the 10-15 minute time period, if the pH is still less than 6.8, $CO_{2i}$ is adjusted to allow pH to increase at a rate of approximately 0.4 pH units/minute, and if tissue pH is greater than 7 then $CO_{2i}$ is adjusted to a slower rate of 0.2 pH units/minute.

Referring to FIG. 2, the ventilator provides for both negative and positive pressures by means of the double venturi 32 such as that described in U.S. Pat. No. 5,664,563. Safety mechanisms are provided by shutoff valve 31 and exhaust valve 28. Heater/humidifier element 33 conditions the gas prior to entering the inspiration circuit, and capnometric measurements are determined using the capnometric sensor 22 and tidal volume sensor 21.

Referring again to FIGS. 3A and 3B, by measuring both flow rates and the $CO_2$ concentration (partial pressure), the quantity of $CO_2$ for the inspiration and expiration cycle can be tracked by integrating the $CO_2$ flow. Though the amount of excess $CO_2$ may be unknown, the amount of $CO_2$ transferred from the bloodstream to the alveoli can be accurately controlled by measuring the difference in $CO_2$ volume on the inspired and expired cycles. Thus to achieve constant $CO_2$ levels, $CO_{2i}$ is increased to the level such is that the volumes of $CO_2$ on inspired and expired cycles are equal. Volumetric measurements for the inspired and expired cycles may be averaged over several cycles to increase accuracy.

In other implementations, either the tissue $CO_2$ or pH are measured by such methods as disclosed in U.S. Pat. No. 6,055,447, which describes a sublingual tissue $CO_2$ sensor, or U.S. Pat. Nos. 5,813,403, 6,564,088, and 6,766,188, which describe a method and device fir measuring tissue pH via near infrared spectroscopy (NIRS). NIRS technology allows the simultaneous measurement of tissue $PO_2$, $PCO_2$, and pH. One drawback of previous methods for the measurement of tissue pH is that the measurements provided excellent relative accuracy for a given baseline measurement performed in a series of measurements over the course of a resuscitation, but absolute accuracy was not as good, as a result of patient-specific offsets such as skin pigment. One of the benefits of the currently-described implementations is that they do not require absolute accuracy of these pH measurements, only that the offset and gain be stable over the course of the resuscitation. Because tissue pH responds slowly over the course of multiple ventilation cycles, it is used primarily to augment control of $E_tCO_2$ levels by adjusting $CO_{2i}$ with the goal of regulating tissue pH per the following regimen: (1) during the first 5 minutes following ROSC, the pH should remain flat; (2) during the time period of 5-10 minutes, the tissue pH should increase no more than 0.4 pH units/minute, and should be limited to not increase above an absolute number of 6.8; and (3) during the 10-15 minute time period, if the pH is still less than 6.8, $CO_{2i}$ is adjusted to allow pH to increase at a rate of approximately 0.4 pH units/minute, and if tissue pH is greater than 7 then $CO_{2i}$ is adjusted to a slower rate of 0.2 pH units/minute.

In some cases, such as cardiac arrest cases with shorter periods of ischemia, it may be desirable to reduce pH levels below the levels present in the cardiac arrest victim by augmenting $CO_2$ levels. In such cases, pH would be decreased during phase 1 of the regimen described in the previous paragraph.

Tissue $CO_2$, and thus pH, as well, are adjusted by increasing or decreasing inspired $CO_2$ levels via the $CO_{2i}^H$ and $CO_{2i}^L$ levels; for instance, decreasing both levels will cause additional $CO_2$ to be exhaled, thus reducing tissue pH. Adjustments are made in approximately 10% increments at approximately 3 times per minute. The low update rate of $CO_{2i}^H$ and $CO_{2i}^L$ levels is due to the fact that the time constant for pH changes due to $CO_{2i}$ changes is slow as well.

In other implementations, medical knowledge such as that described in Crit Care Med 2000 Vol. 28, No, 11 (Suppl.) is incorporated into a closed loop feedback system to augment the methods described above for controlling tissue pH during resuscitation. As the author describes, the system of differential equations has been described in a number of publications. In this specific instance, "the human circulation is represented by seven compliant chambers, connected by resistances through which blood may flow. The compliances correspond to the thoracic aorta, abdominal aorta, superior vena cava and right heart, abdominal and lower extremity veins, carotid arteries, and jugular veins. In addition, the chest compartment contains a pump representing the pulmonary vascular and left heart compliances. This pump may be configured to function either as a heart-like cardiac pump, in which applied pressure squeezes blood from the heart itself through the aortic valve, or as a global thoracic pressure pump, in which applied pressure squeezes blood from the pulmonary vascular bed, through the left heart, and into the periphery. Values for physiologic variables describing a textbook normal '70-kg man' are used to specify compliances and resistances in the model. The distribution of vascular conductances (1/resistances) into cranial, thoracic, and caudal components reflects textbook distributions of cardiac output to various body regions." In addition to these equations, implementations may incorporate inspiratory volumetric measurement and the universal alveolar airway equation, the Henderson-Hasselbalch equation, and a three-compartment model of carbon dioxide storage in the body. The compartment with the lowest time constant corresponds to the well-perfused organs of brain, blood, kidneys, heart; the second compartment corresponds to skeletal muscle; and the third compartment corresponds to all other tissue.

Referring to FIG. 5, a closed loop feedback method is employed, using state space methods with the system estimation block 55 provided by a physiological model as described above with augmentations to include $CO_2$ and pH effects. The Feedback Controller 53 may employ such traditional control system methods as proportional, difference, integral (PID) or state feedback control methods, known to those skilled in the art.

Since the caiac arrest victim is spontaneously breathing during ROSC, and the central chemoreceptors will be stimulated by the elevated $CO_2$ levels and depressed pH, it is necessary for the ventilator to respond to the victim's own inspiratory efforts. Pressure sensing is used to determine patient respiratory effort. A combination of synchronized intermittent mandatory ventilation (SIMV) and inspiratory pressure support ventilation (PSV) are used to provide proper responsiveness to victim respiratory needs while at the same time providing a sufficient amount of minute ventilation so that $pCO_2$ can be regulated via $CO_{2i}$. SIMV allows the victim to take breaths between artificial breaths and PSV assists the victim in making an inspiration of a pattern that is largely of their own control. With PSV, the amount of support is variable, with more support being provided in the early stages of ROSC and the support gradually reduced as the victim's status improves during the course of ROSC.

The drug infuser 18 may be used to deliver other agents such as glutamate, aspartate or other metabolically active agents that may be particularly effective during the pH-depressed reperfusion state of the invention in renormalizing lactate levels and generating the ATP stores necessary to restore cytosolic calcium homeostasis prior to allowing pH to increase.

The chest compressor 12 and ventilator 15 may be physically separate from the defibrillator, and the physiological monitor 10 and control of the chest compressor 12 and ventilator 15 may be accomplished by a communications link 16. The communications link 16 may take the form of a cable connecting the devices but preferably the link 16 is via a wireless protocol such as Bluetooth or a wireless protocol such as Institute of Electrical and Electronics Engineers (IEEE) 802.11. The separate chest compressor 12 and can be a portable chest compression device such as that commercially available as the Autopulse™, provided by ZOLL Circulatory Systems of Sunnyvale Calif. The separate ventilator 15 can be a ventilator such as that is commercially available as the iVent™, provided by Versamed of Peal River, N.Y. The separate drug infuser 18 can be a drug infusion device such as that commercially available as the Power Infuser™, provided by Infusion Dynamics of Plymouth Meeting, Pa., or the Colleague CX™, provided by Baxter Healthcare Corp., of Round Lake, Ill. The chest compressor 12, ventilator 15, drug infuser 18, and defibrillator 13 can also be integrated into one housing such as that for the Autopulse™, provided by ZOLL Circulatory Systems of Sunnyvale, Calif.

In other implementations, control and coordination for the overall resuscitation event and the delivery of the various therapies may be accomplished by a device 17 or processing element external to either the chest compressor, ventilator, or defibrillator. For instance the device 17 may be a laptop computer or other handheld computer or a dedicated computing device that will download and process the ECG data from the defibrillator, analyze the ECG signals, perform the determinations based on the analysis, and control the other therapeutic devices, including the defibrillator 13. While the system has been described for cardiac arrest, it is also applicable for trauma victims or other forms of arrest where the victim is suffering, from amongst other conditions, a global ischemia, and resuscitation from which requires the patient to transition through a state of reperfusion.

Many other implementations of the invention other than those described above are within the invention, which is defined by the following claims. References to "processing" in the claims include a microprocessor (and associated memory and hardware) executing software.

What is claimed is:

1. A method for providing resuscitation treatment to a patient in cardiac arrest with a ventilator, the method comprising: receiving at least two measurements of a CO2 concentration in an airway of the patient; receiving a signal indicative that return of spontaneous circulation (ROSC) in the patient has occurred; processing the at least two measurements of the CO2 concentration in the airway of the patient; and adjusting a partial pressure of CO2 of an inspiratory gas mixture delivered via the ventilator, based at least in part on the at least two measurements of the CO2 concentration, to slow expiration of CO2 from lungs of the patient and to maintain a low pH in a tissue of the patient for a period of time following ROSC, wherein the adjusting of the partial pressure of CO2 includes determining a change of a partial pressure of CO2 gas in the inspiratory gas mixture from a first partial pressure to one or more second partial pressures high enough to slow expiration of CO2 from the lungs of the patient to thereby maintain the low pH in the tissue of the patient, wherein the low pH is approximately at or below a pH level present in the tissue subsequent to an adverse cardiac event and immediately prior to ROSC.

2. The method of claim 1, wherein receiving the at least two measurements of the CO2 concentration include measuring the CO2 concentration via at least one first sensor.

3. The method of claim 1, wherein said adjusting the partial pressure of CO2 is based at least in part on a measured pH in the tissue of the patient.

4. The method of claim 3, comprising receiving one or more signals indicative of a concentration of CO2 in a tissue of the patient and processing the one or more signals indicative of the concentration of CO2 of the tissue of the patient to provide a measurement of the concentration of CO2 in the tissue of the patient, wherein said receiving the one or more signals indicative of the concentration of CO2 of the tissue of the patient comprises measurement, via at least one second sensor to measure the pH in the tissue in the patient.

5. The method of claim 1, wherein the low pH in the tissue of the patient comprises a pH below 7.0 during the period of time following ROSC.

6. The method of claim 1, wherein said adjusting the partial pressure of $CO_2$ includes maintaining the pH in the tissue of the patient at a substantially constant level for a first portion of the period of time following ROSC.

7. The method of claim 6, wherein the period of time is a predetermined period of time, and wherein said adjusting the partial pressure of $CO_2$ impacts the pH in the tissue of the patient for the predetermined period of time following ROSC.

8. The method of claim 7, wherein:
said adjusting the partial pressure of $CO_2$ includes increasing the pH in the tissues at a first rate during a second portion of the predetermined period of time following ROSC, wherein the second portion of the period of time following ROSC is subsequent to the first portion of the period of time;
the first rate comprises no more than 0.4 pH units/minute;
an absolute value of the pH in the tissue at an end of the second portion of the period of time is no more than 6.8;
said adjusting the partial pressure of $CO_2$ includes an increase in the pH in the tissue at a second rate during a third portion of the predetermined period of time, wherein the third portion of the period of time is subsequent to the second portion of the period of time;
said adjusting the partial pressure of $CO_2$ is such that, when the pH during the third portion of the period of time is less than 6.8, the second rate comprises approximately 0.4 pH units/minute or less, and, when the pH during the third portion of the period of time is greater than 7, the second rate comprises approximately 0.2 pH units/minutes or less; and
each of the first portion, the second portion, and the third portion of the period of time comprises up to five minutes.

9. The method of claim 1, further comprising adjusting the inspiratory gas mixture via one or more valves of the ventilator.

10. The method of claim 9, further comprising adjusting the inspiratory gas mixture via the one or more valves of the ventilator to add $CO_2$ to the inspiratory gas mixture, and comprising electronically controlling the one or more valves at least in response to ROSC.

11. The method of claim 1, wherein the ventilator includes a user interface configured to receive input indicating that ROSC has occurred.

12. A method for providing resuscitation treatment to a patient in cardiac arrest with a ventilator, the method comprising:
receiving at least two measurements of a $CO_2$ concentration in an airway of the patient;
receiving an input of whether return of spontaneous circulation (ROSC) in the patient has occurred, wherein said receiving an input of whether return of ROSC in the patient has occurred comprises a patient monitor determining whether ROSC has occurred based on a comparison of the at least two measurements of the $CO_2$ concentration in the airway of the patient;
processing the at least two measurements of the $CO_2$ concentration in the airway of the patient; and
adjusting a partial pressure of $CO_2$ of an inspiratory gas mixture delivered via the ventilator, based at least in part on the at least two measurements of the $CO_2$ concentration, to slow expiration of $CO_2$ from lungs of the patient and to maintain a low pH in a tissue of the patient for a period of time following ROSC.

13. The method of claim 12, wherein said receiving the at least two measurements of the $CO_2$ concentration include measuring the $CO_2$ concentration via at least one first sensor.

14. The method of claim 12, wherein said adjusting the partial pressure of $CO_2$ is based at least in part on a measured pH in the tissue of the patient.

15. The method of claim 14, comprising receiving one or more signals indicative of a concentration of $CO_2$ in a tissue of the patient and processing the one or more signals indicative of the concentration of $CO_2$ of the tissue of the patient to provide a measurement of the concentration of $CO_2$ in the tissue of the patient, wherein said receiving the one or more signals indicative of the concentration of $CO_2$ of the tissue of the patient comprises measurement, via at least one second sensor to measure the pH in the tissue in the patient.

16. The method of claim 12, wherein the low pH in the tissue of the patient comprises a pH below 7.0 during the period of time following ROSC.

17. The method of claim 12, wherein said adjusting the partial pressure of $CO_2$ includes maintaining the pH in the tissue of the patient at a substantially constant level for a first portion of the period of time following ROSC.

18. The method of claim 17, wherein the period of time is a predetermined period of time, and wherein said adjusting the partial pressure of $CO_2$ impacts the pH in the tissue of the patient for the predetermined period of time following ROSC.

19. The method of claim 18, wherein:
said adjusting the partial pressure of $CO_2$ includes increasing the pH in the tissues at a first rate during a second portion of the predetermined period of time following ROSC, wherein the second portion of the period of time following ROSC is subsequent to the first portion of the period of time;
the first rate comprises no more than 0.4 pH units/minute;
an absolute value of the pH in the tissue at an end of the second portion of the period of time is no more than 6.8;
said adjusting the partial pressure of $CO_2$ includes an increase in the pH in the tissue at a second rate during a third portion of the predetermined period of time, wherein the third portion of the period of time is subsequent to the second portion of the period of time;
said adjusting the partial pressure of $CO_2$ is such that, when the pH during the third portion of the period of time is less than 6.8, the second rate comprises approximately 0.4 pH units/minute or less, and, when the pH during the third portion of the period of time is greater than 7, the second rate comprises approximately 0.2 pH units/minutes or less; and
each of the first portion, the second portion, and the third portion of the period of time comprises up to five minutes.

20. The method of claim 12, further comprising adjusting the inspiratory gas mixture via one or more valves of the ventilator.

21. The method of claim 20, further comprising adjusting the inspiratory gas mixture via the one or more valves of the ventilator to add $CO_2$ to the inspiratory gas mixture, and comprising electronically controlling the one or more valves at least in response to ROSC.

22. A method for providing resuscitation treatment to a patient in cardiac arrest with a ventilator, the method comprising:
receiving at least two measurements of a CO2 concentration in an airway of the patient;
receiving a signal indicative that return of spontaneous circulation (ROSC) in the patient has occurred, wherein receiving the signal that ROSC in the patient has occurred includes a rescuer providing an input via a user interface of a device;
processing the at least two measurements of the CO2 concentration in the airway of the patient; and
adjusting a partial pressure of CO2 of an inspiratory gas mixture delivered via the ventilator, based at least in part on the at least two measurements of the CO2 concentration, to slow expiration of CO2 from lungs of the patient and to maintain a low pH in a tissue of the patient for a period of time following ROSC.

23. The method of claim 22, wherein said receiving the at least two measurements of the CO2 concentration include measuring the CO2 concentration via at least one first sensor.

24. The method of claim 22, wherein said adjusting the partial pressure of CO2 is based at least in part on a measured pH in the tissue of the patient.

25. The method of claim 24, comprising receiving one or more signals indicative of a concentration of CO2 in a tissue of the patient and processing the one or more signals indicative of the concentration of CO2 of the tissue of the patient to provide a measurement of the concentration of CO2 in the tissue of the patient, wherein said receiving the one or more signals indicative of the concentration of CO2 of the tissue of the patient comprises measurement, via at least one second sensor to measure the pH in the tissue in the patient.

26. The method of claim 22, wherein the low pH in the tissue of the patient comprises a pH below 7.0 during the period of time following ROSC.

27. The method of claim 22, wherein said adjusting the partial pressure of CO2 includes maintaining the pH in the tissue of the patient at a substantially constant level for a first portion of the period of time following ROSC.

28. The method of claim 27, wherein the period of time is a predetermined period of time, and wherein said adjusting the partial pressure of CO2 impacts the pH in the tissue of the patient for the predetermined period of time following ROSC.

29. The method of claim 28, wherein:
said adjusting the partial pressure of CO2 includes increasing the pH in the tissues at a first rate during a second portion of the predetermined period of time following ROSC, wherein the second portion of the period of time following ROSC is subsequent to the first portion of the period of time;
the first rate comprises no more than 0.4 pH units/minute;
an absolute value of the pH in the tissue at an end of the second portion of the period of time is no more than 6.8;
said adjusting the partial pressure of CO2 includes an increase in the pH in the tissue at a second rate during a third portion of the predetermined period of time, wherein the third portion of the period of time is subsequent to the second portion of the period of time;
said adjusting the partial pressure of CO2 is such that, when the pH during the third portion of the period of time is less than 6.8, the second rate comprises approximately 0.4 pH units/minute or less, and, when the pH during the third portion of the period of time is greater than 7, the second rate comprises approximately 0.2 pH units/minutes or less; and
each of the first portion, the second portion, and the third portion of the period of time comprises up to five minutes.

30. The method of claim 22, further comprising adjusting the inspiratory gas mixture via one or more valves of the ventilator.

31. The method of claim 30, further comprising adjusting the inspiratory gas mixture via the one or more valves of the ventilator to add CO2 to the inspiratory gas mixture, and comprising electronically controlling the one or more valves at least in response to ROSC.

32. The method of claim 22, wherein said receiving the signal that ROSC in the patient has occurred includes the rescuer providing the input via the user interface of the device, wherein the device comprises the ventilator.

33. A method for providing resuscitation treatment to a patient in cardiac arrest with a ventilator, the method comprising:
receiving at least two measurements of a CO2 concentration in an airway of the patient;
receiving a signal return of spontaneous circulation (ROSC) in the patient has occurred;
processing the at least two measurements of the CO2 concentration in the airway of the patient;
adjusting a partial pressure of CO2 of an inspiratory gas mixture delivered via the ventilator, based at least in part on the at least two measurements of the CO2 concentration, to slow expiration of CO2 from lungs of the patient and to maintain a low pH in a tissue of the patient for a period of time following ROSC, wherein the low pH in the tissue of the patient comprises a pH of less than 7.0;
wherein said adjusting the partial pressure of CO2 includes maintaining the pH in the tissue of the patient at a substantially constant level for a first portion of the period of time following ROSC;
wherein the period of time is a predetermined period of time, and wherein said adjusting the partial pressure of CO2 impacts the pH in the tissue of the patient for the predetermined period of time following ROSC;
said adjusting the partial pressure of CO2 includes increasing the pH in the tissues at a first rate during a second portion of the predetermined period of time following ROSC, wherein the second portion of the period of time following ROSC is subsequent to the first portion of the period of time;
the first rate comprises no more than 0.4 pH units/minute;
an absolute value of the pH in the tissue at an end of the second portion of the period of time is no more than 6.8;
said adjusting the partial pressure of CO2 includes an increase in the pH in the tissue at a second rate during a third portion of the predetermined period of time, wherein the third portion of the period of time is subsequent to the second portion of the period of time;
said adjusting the partial pressure of CO2 is such that, when the pH during the third portion of the period of time is less than 6.8, the second rate comprises approximately 0.4 pH units/minute or less, and, when the pH during the third portion of the period of time is greater than 7, the second rate comprises approximately 0.2 pH units/minutes or less; and
each of the first portion, the second portion, and the third portion of the period of time comprises up to five minutes.

34. The method of claim 33, wherein said receiving the at least two measurements of the CO2 concentration include measuring the CO2 concentration via at least one first sensor.

35. The method of claim 33, wherein said adjusting the partial pressure of CO2 is based at least in part on a measured pH in the tissue of the patient.

36. The method of claim 35, comprising receiving one or more signals indicative of a concentration of CO2 in a tissue of the patient and processing the one or more signals indicative of the concentration of CO2 of the tissue of the patient to provide a measurement of the concentration of CO2 in the tissue of the patient, wherein said receiving the one or more signals indicative of the concentration of CO2 of the tissue of the patient comprises measurement, via at least one second sensor to measure the pH in the tissue in the patient.

37. The method of claim 33, further comprising adjusting the inspiratory gas mixture via one or more valves of the ventilator.

38. The method of claim 37, further comprising adjusting the inspiratory gas mixture via the one or more valves of the ventilator to add CO2 to the inspiratory gas mixture, and comprising electronically controlling the one or more valves at least in response to ROSC.

39. The method of claim 33, wherein the ventilator includes a user interface configured to receive input indicating that ROSC has occurred.

40. The method of claim 33, wherein the low pH comprises a pH of between approximately 6.5 and 6.8.

* * * * *

UNITED STATES PATENT AND TRADEMARK OFFICE
CERTIFICATE OF CORRECTION

PATENT NO. : 11,219,737 B2
APPLICATION NO. : 16/058592
DATED : January 11, 2022
INVENTOR(S) : Gary A. Freeman and Elizabeth E. Silver It is certified that error appears in the above-identified patent and that said Letters Patent is hereby corrected as shown below:

On the Title Page
Column 2, Line 3 (Other Publications) - delete "Grit", insert -- Crit --

In the Claims
Claim 4, Column 12, Line 66 - delete "tissue in", insert -- tissue of --
Claim 15, Column 14, Line 19 - delete "sensor", insert -- sensor, --
Claim 15, Column 14, Line 19 - delete "tissue in", insert -- tissue of --
Claim 25, Column 15, Line 34 - delete "tissue in", insert -- tissue of --
Claim 33, Column 16, Line 24 - after "receiving a signal", insert -- indicative that --
Claim 36, Column 17, Line 16 - delete "sensor", insert -- sensor, --
Claim 36, Column 17, Line 16 - delete "tissue in", insert -- tissue of --

Signed and Sealed this
Third Day of May, 2022

Katherine Kelly Vidal
*Director of the United States Patent and Trademark Office*